US008202275B2

(12) United States Patent
Wozencroft

(10) Patent No.: US 8,202,275 B2
(45) Date of Patent: Jun. 19, 2012

(54) CAP AND ACTIVATION TOOL

(75) Inventor: Robert Michael Wozencroft, Epsom (GB)

(73) Assignee: Finsbury (Development) Limited, Leatherhead, Surrey (GB)

( * ) Notice: Subject to any disclaimer, the term of this patent is extended or adjusted under 35 U.S.C. 154(b) by 724 days.

(21) Appl. No.: 11/224,775

(22) Filed: Sep. 13, 2005

(65) Prior Publication Data
US 2006/0058885 A1  Mar. 16, 2006

(51) Int. Cl.
*A61B 17/56* (2006.01)
(52) U.S. Cl. ............................................. 606/91
(58) Field of Classification Search ............... 606/99, 606/91, 100, 81, 86 R; 623/22.21–22.39
See application file for complete search history.

(56) References Cited

U.S. PATENT DOCUMENTS

| 4,351,466 | A |   | 9/1982  | Noiles |  |
|-----------|---|---|---------|--------|--|
| 4,865,600 | A | * | 9/1989  | Carpentier et al. | 623/2.11 |
| 5,100,417 | A | * | 3/1992  | Cerier et al. | 606/139 |
| 5,207,674 | A | * | 5/1993  | Hamilton | 606/20 |
| 5,411,506 | A | * | 5/1995  | Goble et al. | 606/104 |
| 5,484,440 | A | * | 1/1996  | Allard | 606/916 |
| 5,549,618 | A |   | 8/1996  | Fleenor et al. |  |
| 5,556,407 | A | * | 9/1996  | Wurster et al. | 606/174 |
| 5,669,917 | A | * | 9/1997  | Sauer et al. | 606/139 |
| 5,669,919 | A |   | 9/1997  | Sanders et al. |  |
| 5,752,964 | A |   | 5/1998  | Mericle |  |
| 5,826,594 | A | * | 10/1998 | Sokal | 132/200 |
| 5,976,148 | A | * | 11/1999 | Charpenet et al. | 606/91 |
| 5,984,959 | A | * | 11/1999 | Robertson et al. | 623/2.11 |
| 6,096,074 | A | * | 8/2000  | Pedros | 623/2.1 |
| 6,214,043 | B1 | * | 4/2001 | Krueger et al. | 623/2.11 |
| 6,254,620 | B1 | * | 7/2001 | Koh et al. | 606/167 |
| 6,319,280 | B1 | * | 11/2001 | Schoon | 623/2.11 |
| 6,451,058 | B2 | * | 9/2002 | Tuke et al. | 623/22.21 |
| 6,589,284 | B1 | * | 7/2003 | Silberer | 623/22.29 |
| 6,679,895 | B1 | * | 1/2004 | Sancoff et al. | 606/144 |
| 6,746,452 | B2 | * | 6/2004 | Tuke et al. | 606/91 |
| 7,094,246 | B2 | * | 8/2006 | Anderson et al. | 606/148 |
| 7,144,398 | B2 | * | 12/2006 | Chern Lin et al. | 606/92 |
| 7,232,455 | B2 | * | 6/2007 | Pedlick et al. | 606/232 |
| 2002/0007708 | A1 | * | 1/2002 | Freeman | 83/36 |
| 2002/0177854 | A1 | * | 11/2002 | Tuke et al. | 606/91 |
| 2003/0125805 | A1 |   | 7/2003 | Johnson et al. |  |
| 2003/0156376 | A1 | * | 8/2003 | Nitoh et al. | 361/301.3 |
| 2004/0122450 | A1 |   | 6/2004 | Oren et al. |  |
| 2004/0148017 | A1 |   | 7/2004 | Stobie |  |
| 2004/0186569 | A1 | * | 9/2004 | Berry | 623/17.11 |
| 2005/0092142 | A1 | * | 5/2005 | Nish | 81/452 |
| 2006/0259043 | A1 | * | 11/2006 | Miyamoto et al. | 606/139 |

FOREIGN PATENT DOCUMENTS

GB    2 323 036 A    9/1998
WO    WO 04/000172 A1    12/2003

OTHER PUBLICATIONS

European Search Report for Application No. EP 05108359.0-2310 dated Nov. 14, 2005, 5 pages.

* cited by examiner

*Primary Examiner* — Eduardo C Robert
*Assistant Examiner* — Jerry Cumberledge
(74) *Attorney, Agent, or Firm* — Senniger Powers LLP

(57) ABSTRACT

A cap for use during the insertion of a prosthesis comprising: an impaction plate; an least one cable loop for connecting the impaction plate to a prosthesis; clamping means for attaching the at least one cable means to the impaction plate; and cutting means for severing the at least one loop at one point along its length.

30 Claims, 21 Drawing Sheets

CAP AND ACTIVATION TOOL

BACKGROUND OF THE INVENTION

The present invention relates to a cap for a prosthetic implant and to an activation tool for use therewith.

The replacement of all or a part of the bone surface of an articulation with a prosthetic implant has become a common surgical procedure. The procedure requires the surgeon to exercise both precision and delicacy in the placement of the prosthetic implant. However, it is frequently necessary for the surgeon also to exercise a degree of force, sometimes a vigorous force, in order to situate the prosthetic implant in the desired location on the bone surface.

For example, in an operation to insert a prosthetic acetabulum in a patient's pelvis the surgeon first uses a reamer to grind a cavity of appropriate size in the patient's pelvis. An acetabular cup is then inserted into the cavity. By "appropriate size" is meant a size which is selected by the surgeon as being the most appropriate for that particular patient. Normally, it is desirable to retain as much of the original healthy bone surface as possible.

Commercially available acetabular cups are sold in a range of sizes to suit the needs of individual patients. Generally, acetabular cups are available in sizes of from 42 mm to 62 mm diameter, with 2 mm increments between neighbouring sizes.

There are a number of different types of prosthetic acetabular cups. One type of cup is those made from polyethylene. These are generally cemented into the acetabulum and require only light pressure to seat them in the cement. One alternative cup type has a polyethylene liner unit for articulation with the femur and a metal shell for insertion into the pelvic cavity. These cups with metal shells may be implanted without cement such that they rely on a jam fit between the metal shell and the patient's acetabulum. Often these metal shells have outer surfaces or coatings which encourage bone to grow into them over time. With this type of prosthesis, the polyethylene liner unit is snapped or screwed into the metal shell after the metal shell has been seated in the acetabulum to form the socket part of the joint.

Prosthetic acetabular cups generally require the use of an insertion tool to achieve correct positioning of the prosthesis in the patient's pelvic cavity. Cups which rely on a jam fit require a greater force to be applied via the insertion tool than is the case with cemented polyethylene cups. This force is usually a direct impact into the acetabulum, but force may also be applied to adjust the angular position of the cup or to remove the cup if it has been positioned incorrectly.

In order that the required forces are accurately and safely applied to the cup, it is generally necessary that the insertion tool positively grips the cup. However, it is also important that the means by which the tool grips the cup does not impinge upon the outside of the metal shell in order that in use the insertion tool does not become trapped between the shell and the pelvic bone. Further, as the wall thickness of the shell is generally kept to a minimum, the tool cannot generally grip the wall. Insertion tools are therefore generally designed to grip on a mechanical feature provided on the inner hemisphere of the metal shell. This feature is usually designed so as to cause minimum compromise to the function of the prosthetic hip joint. As a result it is often not strong enough for the impaction forces applied which may result in damage to the insertion tool, the metal shell or both.

As acetabular cups are available in a range of sizes, the tools conventionally used to insert them must similarly be provided in a range of sizes such that they can correctly fit and engage with the features provided on the cups. Having to purchase a range of such tools has cost implications for hospitals.

A third category of prosthetic hip joint exists which is manufactured entirely from metal so that the prosthetic articulation comprises a metal on metal joint. These are usually implanted without cement, relying on a jam fit in the acetabulum. With this type of cup the inner hemisphere is not a convenient place to locate a mechanical feature on which the insertion tool could grip. First, the presence of any mechanical feature on the inner surface would reduce the surface area of the prosthetic articulation. Secondly, it could cause damage to the highly polished surface of the metal.

It is therefore desirable to provide an insertion system and in particular an insertion tool for a prosthetic implant in which the attachment means between the insertion tool and the prosthesis is sufficiently robust to withstand the impaction and other forces to which it may be subjected during insertion of the prosthesis and which does not compromise the structural strength or the articulating properties of the prosthesis itself.

One solution to the problems of prior art arrangements is described in GB2323036 in which there is described a prosthetic implant which includes means for attaching a cable to the implant. The cable may secure a liner to the implant. A tool is provided which is connected to the implant by means of the cable. Where the liner is present, the connection of the prosthesis to the tool may be via the liner. In use the surgeon may provide force to the tool to cause the implant to be seated in the bone and then the tool is released. In one arrangement the cable is a continuous cable formed into several loops. Once the prosthesis is located in the desired position, it may be necessary to cut the cable to remove it from the prosthesis.

However, whilst this arrangement offers an improvement over prior art devices, there is still a need for alternative arrangements. Further, it is desirable to provide an arrangement in which the cable can be readily cut and removed.

These improvements may be achieved by providing an cap for use with a prosthesis which is held in the prosthesis be means of one or more cables and which includes means for cutting the cable and holding the cut cable such that it is removed when the cap is removed.

Thus according to the present invention there is provided a cap for use during the insertion of a prosthesis comprising:
- an impaction plate;
- an least one cable loop for connecting the impaction plate to a prosthesis;
- clamping means for attaching the at least one cable means to the impaction plate; and
- cutting means for severing the at least one loop at one point along its length.

The impaction plate may be of any suitable configuration but in one arrangement the plate may be configured such that in use it forms a protective cap over substantially the whole of an open face of the prosthesis but does not impinge on the external surface of the prosthesis and therefore does not hamper the insertion of the prosthesis into the bone. It will be understood that the term "plate" covers all suitable configurations and may include those which have a differing cross-section through their depth. The shape of the plate will generally depend on the prosthesis with which the cap is to be used. Where the cap is for use with an acetabular cup prosthesis, it will generally be of a substantially disk configuration which may sit at least partly in the cup.

The cap may include a lip on its upper surface which, in use, extends over at least part of an edge of the prosthesis. The lip may be continuous or, in use, it may extend only over one or more portions of the edge of the prosthesis. Where the prosthesis is an acetabular cup, the impaction plate may extend over at least one or more arcs of the circumference of the rim of the cup.

The impaction plate may be formed from any suitable material. Generally a plastics material such as polyethylene will be used. The material should be suitable to withstand the sterilisation process, be substantially rigid and be able to withstand the impaction forces to which it will be subjected in use.

In one arrangement, the impaction plate may include a neck which extends upwardly from the surface of the impaction plate to surround the clamping and cutting means. The neck may be located centrally of the impaction plate and may surround an aperture in the plate. The neck may be segmented such that arms of the at least one loop may pass between the segments to the clamping means in an arrangement where the clamping means is located in the centre of the neck. The neck may be of a generally frustoconical, annular configuration. The neck may support a platform to which in use an insertion tool may be attached. In arrangements where the tool is attached other than to the platform, the force from the tool may be applied to the platform rather than directly to the surface of the impaction plate.

Whilst the at least one cable loop may extend over the edge of the impaction plate to connect to the prosthesis, the impaction plate will generally include at least one aperture through which the cable passes when forming the at least one cable loop such that the cable can be regarded as passing from the clamping means, through an aperture in the impaction plate, connecting with the prosthesis, returning through the same or a second aperture before returning to the clamping means. It will be understood that this discussion of the cable path is simply to assist understanding and that when the cap of the present invention is actually being assembled, it may follow the procedure detailed above or an alternative procedure may be used. For example, the at least one cable loop may be preformed and then attached to the prosthesis or they may be formed on the prosthesis and then the free ends passed through apertures on the impaction plate to the clamping means.

The or each apertures in the plate maybe slots extending to the edge of the plate or they may be closed apertures such that the cable must be threaded through the aperture. Where there is more than one cable loop present there will generally be at least one aperture associated with each loop.

The or each cable loop will generally connect to the prosthetic implant by any suitable means. In one arrangement, the implant may include a lug around which the cable loop can pass. The lug may extend outwardly from the outer surface of the prosthesis or the rim thereof. The lug may extend substantially perpendicularly from the outer wall of the prosthesis or may be configured such that it is shaped downwardly to form a cleat under which the cable loop may pass.

In one alternative, a track may be provided in the outer wall of the prosthesis in which the cable may be located. The depth of the track will generally be such that when the cable is in position, it will not be proud of the outer surface of the prosthesis. In one preferred arrangement, the track may be generally arcuate such that the ends of the track open to the rim of the prosthesis. In a further alternative arrangement, a bore in the main body portion of the prosthesis may be provided through which the cable can be threaded.

Where more than one cable loop is provided on the cap of the present invention, corresponding attachment means will be provided on the prosthesis for each loop. Generally the same kind of attachment means will be provided for each of the loops on a cap where more than one is present.

Where more than one cable loop is used, they may be formed from a single cable such that the cable having returned to the clamping means to form the first loop will then pass through an aperture, be connected to the prosthesis before returning through the same or a further aperture and returning to the clamping means to form a second loop and so on. Alternatively, each loop may be formed from a separate piece of cable, the ends of which will be clamped by clamping means.

Any number of cable loops maybe used. However, for the stability of the prosthesis when connected to the cap there will generally be three or more cable loops. Where more than one cable loop is present, they are usually spaced substantially evenly around the cap. Similarly, the corresponding attachment means on the prosthesis will be spaced in a corresponding configuration.

The cable from which the each cable loop is formed may be of any suitable size. The diameter of the cable may be quite small, for example from about 0.5 mm to about 2 mm. It will be understood that where the attachment means of the prosthesis is a bore in the wall of the prostheses, a bore suitable to accept cable of from about 0.5 mm to about 2 mm in the rim of a prosthetic acetabulum of cobalt chrome will not compromise the strength of the implant to any serious degree. Similarly, the provision of lugs having sufficient protrusion to allow a cable of from about 0.5 mm to about 2 mm diameter to be looped therearound on the outer surface of the acetabulum, adjacent the rim thereof, will not interfere to any serious degree with the positioning of the implant in the bone cavity. Further a track placed into the outer surface of the wall of the prosthesis of the size which will accept cable of this size will not compromise the strength of the prosthesis.

The cable from which the at least one loop is formed may be of any suitable material. Suitable materials include metals, ceramics, natural fibres or a plastics material. However, when selecting suitable material, it is necessary to ensure that it has the necessary tensile strength. Where the material is metal, stainless steel is particularly preferred. The cable may be single-stranded but is preferably multi-stranded to provide maximum tensile strength per unit weight of material. In one arrangement, the cable loops may be sheathed in a plastics material such as polypropylene.

It will be understood that while the cable loop will generally have a smooth curved profile, the present invention would operate with a loop which has a substantially rectangular profile.

The clamping means and the cutting means maybe separate components or they may be formed from the same component which is capable of carrying out both functions.

In one arrangement the cutting means, may be a guillotine arrangement. That is to say it, or a component of the cutting means, will be movable from a raised non-cutting position to a lowered cutting position. The cutting means may be configured such that when the cap of the present invention is assembled, both arms of at least one the loop pass through the guillotine arrangement. In this configuration, the blade of the guillotine arrangement will be shaped such that it only cuts through one arm so that the other remains hold and held by the clamping means. The blade may be angled such that it is of generally triangular configuration which slopes from a lowest point located above the arm of the loop which is to be cut to a highest non-cutting side which will be located over the arm of the loop which is not to be cut. In an alternative arrangement, the blade may be stepped such that when it is moved downwardly only one arm is cut. In a further alternative arrangement, whilst a frame holding the blade may move downwardly over both arms, the blade may be provided as a tooth in the frame; the tooth being located over the arm of the loop that is to be cut. However, it will be understood that other cutting means may be used provided that only one arm of the at least one loop is cut.

In an arrangement in which more than one cable loop is present but they are formed out of a continuous cable, one arm of each loop may be severed. However, in one alternative, only one loop will be severed such that the cable can be unthreaded but the two ends remained held by the clamping means.

Although the at least one cable loop will generally be cut through one arm, it will be understood that the cap would be configured to enable the cable to be cut at the head of the loop, although this arrangement is not preferred.

The cutting means may be provided at any suitable position on the cap. For convenience, it may be located in the centre of the impaction plate. Where there is more than one loop present, a cutting means maybe provided for each loop. However, generally, a single cutting means will be provided although this will generally include a plurality of blades such that one arm of each loop can be cut. This arrangement may allow one arm of each loop to be cut sequentially or simultaneously.

Any suitable clamping means may be used. In a particularly preferred arrangement, where more than one loop is provided, the clamping means will be located in the centre of the impaction plate such that it can readily retain each loop in place and will take up minimum space on the impaction plate. When the loop as been severed at one point along its length, it will be held by the clamping means such that when the cap is removed from the prosthesis, the cable is removed at the same time.

In a preferred embodiment, the clamping means will be rotatable such that the cable can be wound up into or around the clamping means before the cap is removed from the prosthesis. The clamping means may include a means to enable the user to cause the clamping means to rotate. Thus for example where the clamping means is provided by a nut and bolt arrangement, the user may turn one of the nut or bolt to cause the clamping means to rotate.

The cap may be suitable for use with a range of prosthetic implants and the configuration of the cap will be selected as appropriate for the type of prosthesis.

In a preferred configuration, the cutting means may be an annular arrangement located around the clamping means. In this arrangement, once the cutting means has been operated, the clamping means maybe rotated to draw at least some of the cable into a space between the cutting means and the clamping means The cap of the present invention is particularly suitable for use with an acetabular cup prosthesis.

In order to operate the cutting means a tool may be provided which is shaped to interact with and activate the cutting means. Thus the shaping of the tool will depend on the configuration of the cutting means. In certain arrangements of cap, the tool will cause the cutting means to move downwardly to cut one arm of the loop. Thus in the preferred arrangement detailed above the tool will generally include a substantially annular portion which can be placed over the clamping means to force the cutting means downwardly. The tool preferably includes an engagement formation. The engagement formation will engage with a corresponding formation in the clamping means. This engagement means may enable the user to cause the clamping means to rotate. In one arrangement, the clamping means will include a female engagement formation and a corresponding male engagement formation will be provided on the tool. In an alternative arrangement, the clamping means will include a male engagement formation and a corresponding female engagement formation will be provided on the tool.

In one arrangement, the engagement means may fit around at least a portion of the clamping means and will engage therewith to cause it to rotate.

The engagement formation on the tool may be of any suitable arrangement. Examples of engagement formations which may be provided on the tool includes formations shaped as a screw driver, as a cross-threaded screwdriver or as an Allen key.

Where the engagement formation on the tool is a female engagement formation, it may be a recess which in use can be placed over a male engagement formation on the cap. In one example, the male engagement means is a shaped head, such as a hexagonal head. In this arrangement, the female engagement formation in the tool be a corresponding shape.

In one arrangement, the activation tool may be provided on an introducing tool or as an attachment thereto. The introducing tool may be of any suitable arrangement Thus according to a second aspect of the present invention there is provided an activation tool comprising a handle, means to activate the cutting means and an engagement formation.

The means to activate the cutting means may be an annular ring. Where the tool has a female engagement formation, the rim thereof may also serve as the means to activate the cutting means.

According to a third aspect of the present invention there is provided a prosthesis in combination with the cap of the above first aspect. The prosthesis is preferably an acetabular cup prosthesis.

According to a fourth aspect there is provided a kit of parts comprising one or more of the prosthesis of the above third aspect and at least one activation tool of the above second aspect.

When used, the insert may be disposable or, after provision of replacement cable loops it may be reusable after appropriate sterilisation.

BRIEF DESCRIPTION OF THE DRAWINGS

The present invention will now be described, by way of example, with reference to the following examples in which.

DETAILED DESCRIPTION OF THE PREFERRED EMBODIMENTS

Figure 1:
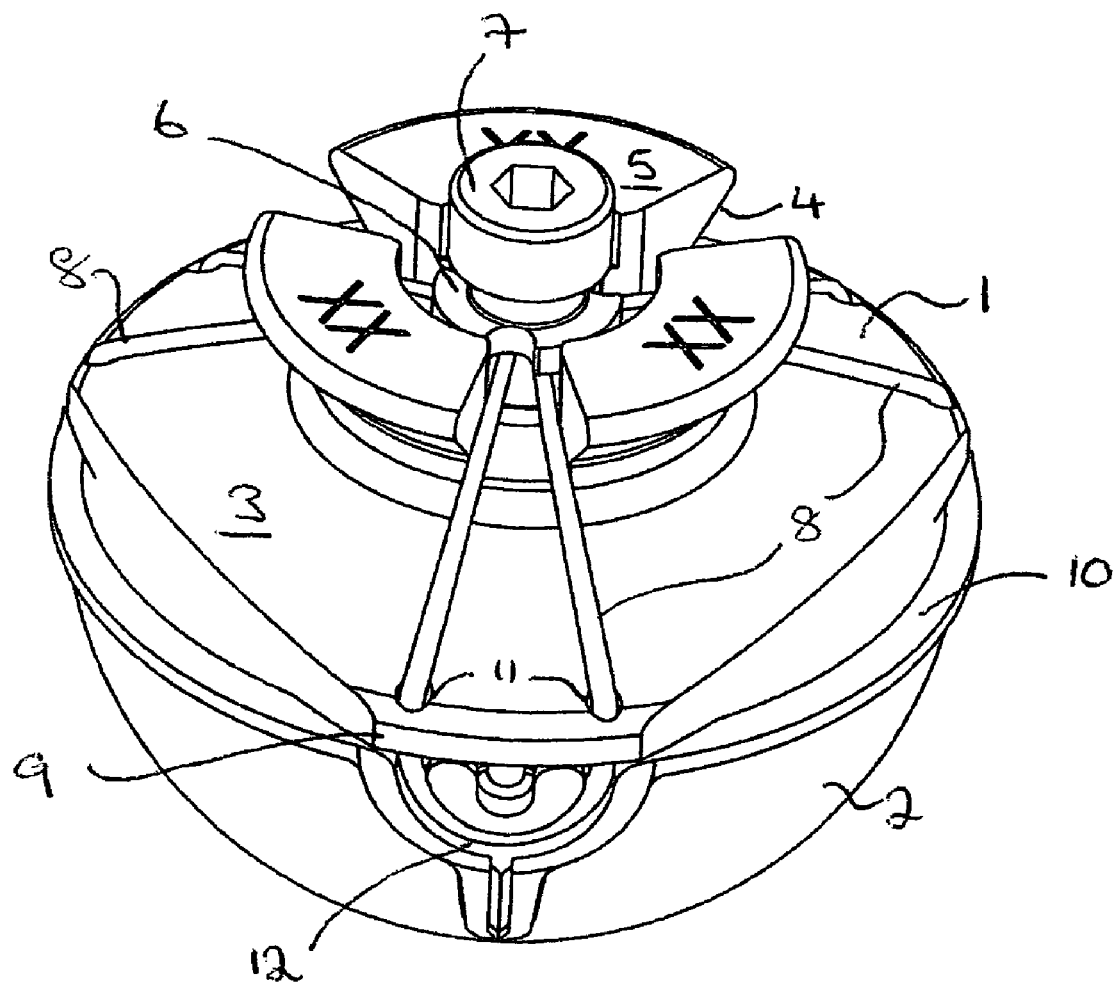
FIG. 1 is a schematic representation of a one preferred arrangement of the present invention in combination with an acetabular cup prosthesis.

As illustrated in FIG. 1, a cap 1 is provided on an acetabular cup prosthesis 2. The cap comprises an impaction plate 3 having a segmented annular frustoconical neck 4 supporting a platform 5. A cutting means 6 and a clamping means 7 are located in the centre of the annular neck 4. Three cable loops 8 extend from the clamping means 7 through the plate 3 and are then connected to the cup 2. The plate 3 includes three lips 9 which extend over portions of the rim 10 of the cup 2. These lips extend over the portion of the cup which includes means for engaging with the cap. The cable loop 8 passes through two apertures 11 and is then placed in a track 12 in a wall of the cup.

Figure 2:
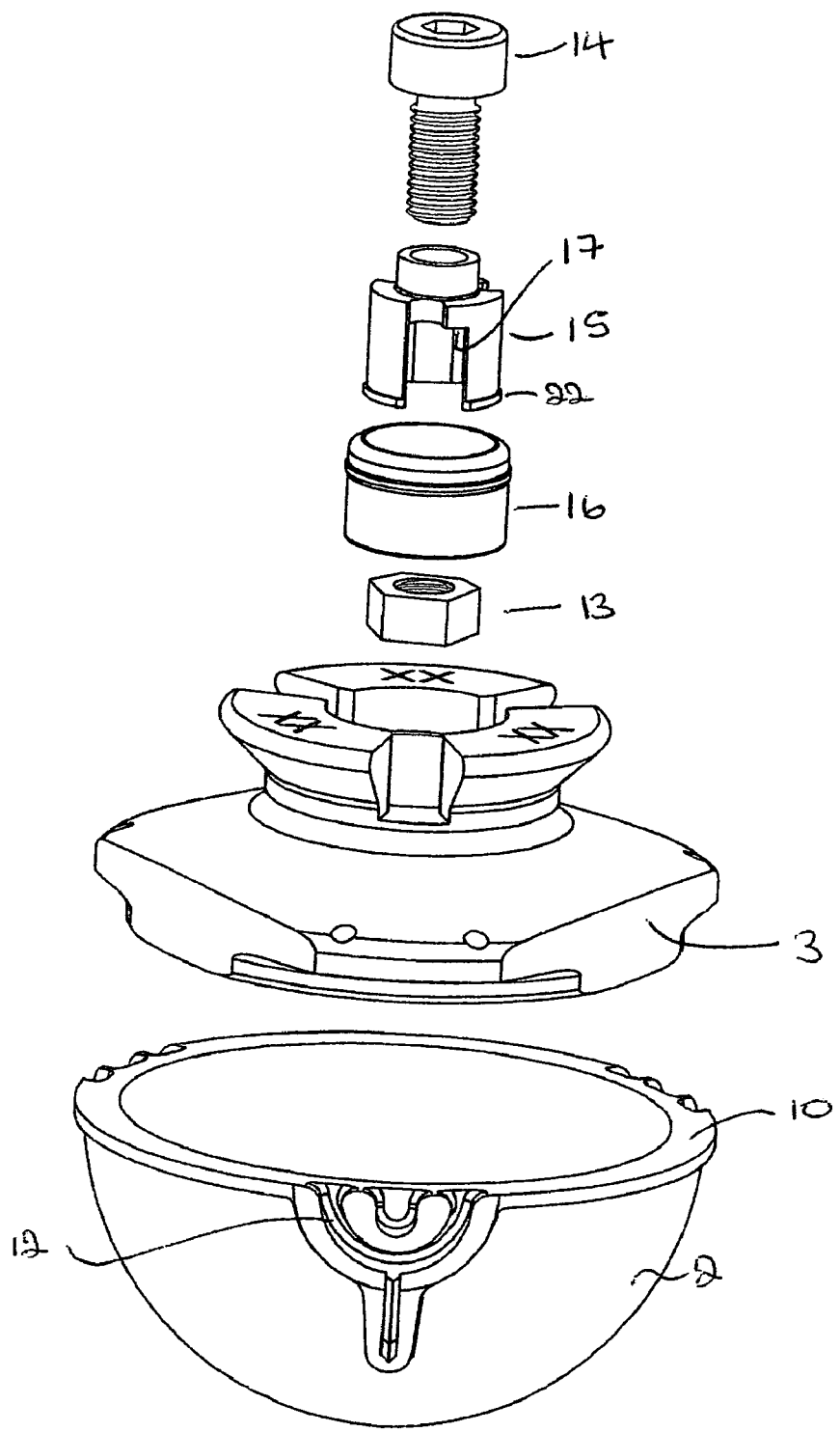
FIG. 2 is an exploded view of the components of the cap of FIG. 1.

As illustrated in more detail in FIG. 2, the acetabular cup 2 includes three spaced annular tracks 12 in the outer wall of the cup which open into the rim 10 of the cup. The clamping means comprises a nut 13 and a bolt 14. These serve to hold the cutting means within the impaction plate 3 and when the cable loops are in position to lock these within the cutting device. The cutting device comprises two components, a guillotine arrangement 15 and a collar 16. The guillotine arrangement is a sliding fit in the collar and has a skirt 22 which prevents it from being pulled through the collar. The guillotine arrangement 15 includes three blades 17 and will also be shaped such that when the guillotine arrangement moves downwardly, only one arm of the loop will be severed. It will be understood that in assembly there may be an aperture in the impaction plate such that the guillotine arrangement sits within the aperture and the bolt is applied from beneath the plate.

During insertion, the insertion tool may connect with the neck 4 such that force is applied to the platform marked XX.

Figure 3:
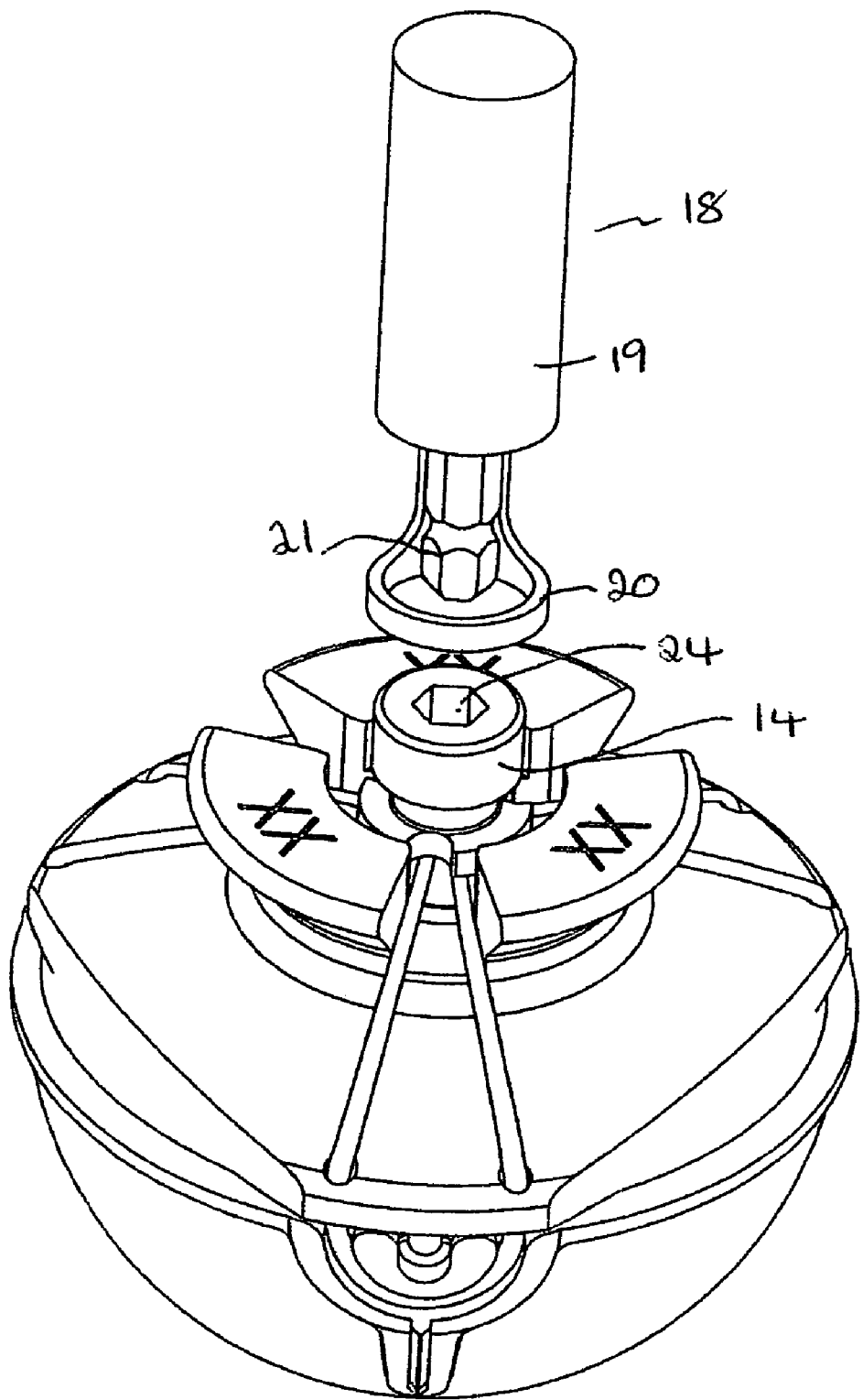
FIG. 3 is a perspective view of the cap of FIG. 1 from above illustrating the tool.

Once the acetabular cup is in the correct position, as illustrated in FIG. 3 the tool 18 which comprises a handle 19, an annular member 20 and an engagement formation 21 is used. In the illustrated arrangement the engagement formation is a male member of hexagonal cross-section to engage with a corresponding formation 24 in the head of the bolt 14.

Figures 4, 5:
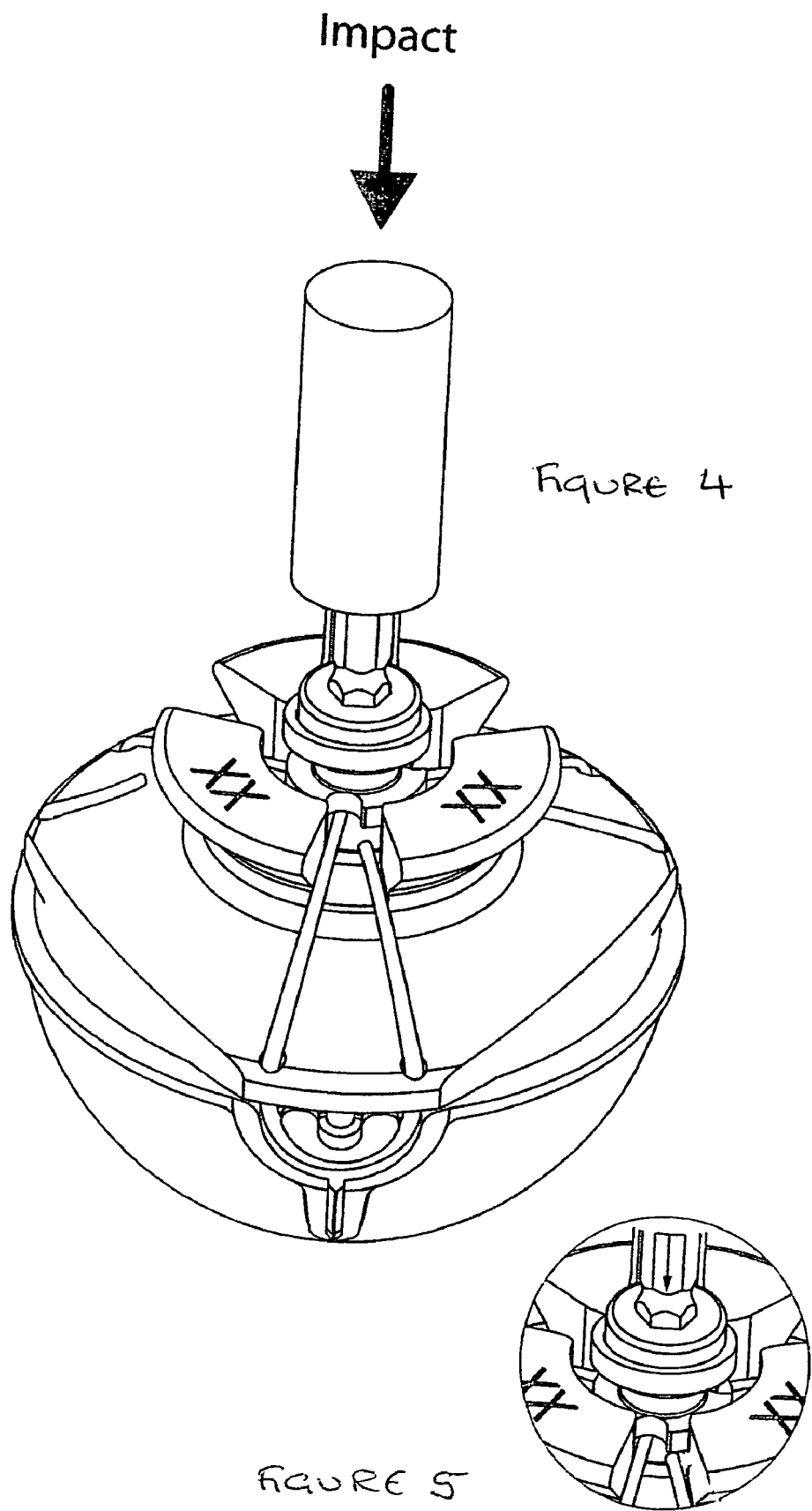
FIG. 4 corresponds to FIG. 3 with the tool engaged.
FIG. 5 represents an exploded view of a portion of FIG. 4 showing the movement of the cutting means on downward pressure on the tool.

As illustrated in FIG. 4, the tool is placed such that the annular member extends around the head of the nut such that a downward impact will force the guillotine member in a downward direction to sever the cable. This is illustrated in more detail in FIG. 5.

Generally the impact required to force the guillotine downwardly may be substantial such that there is no risk of the cable being cut unintentionally.

Figure 6:
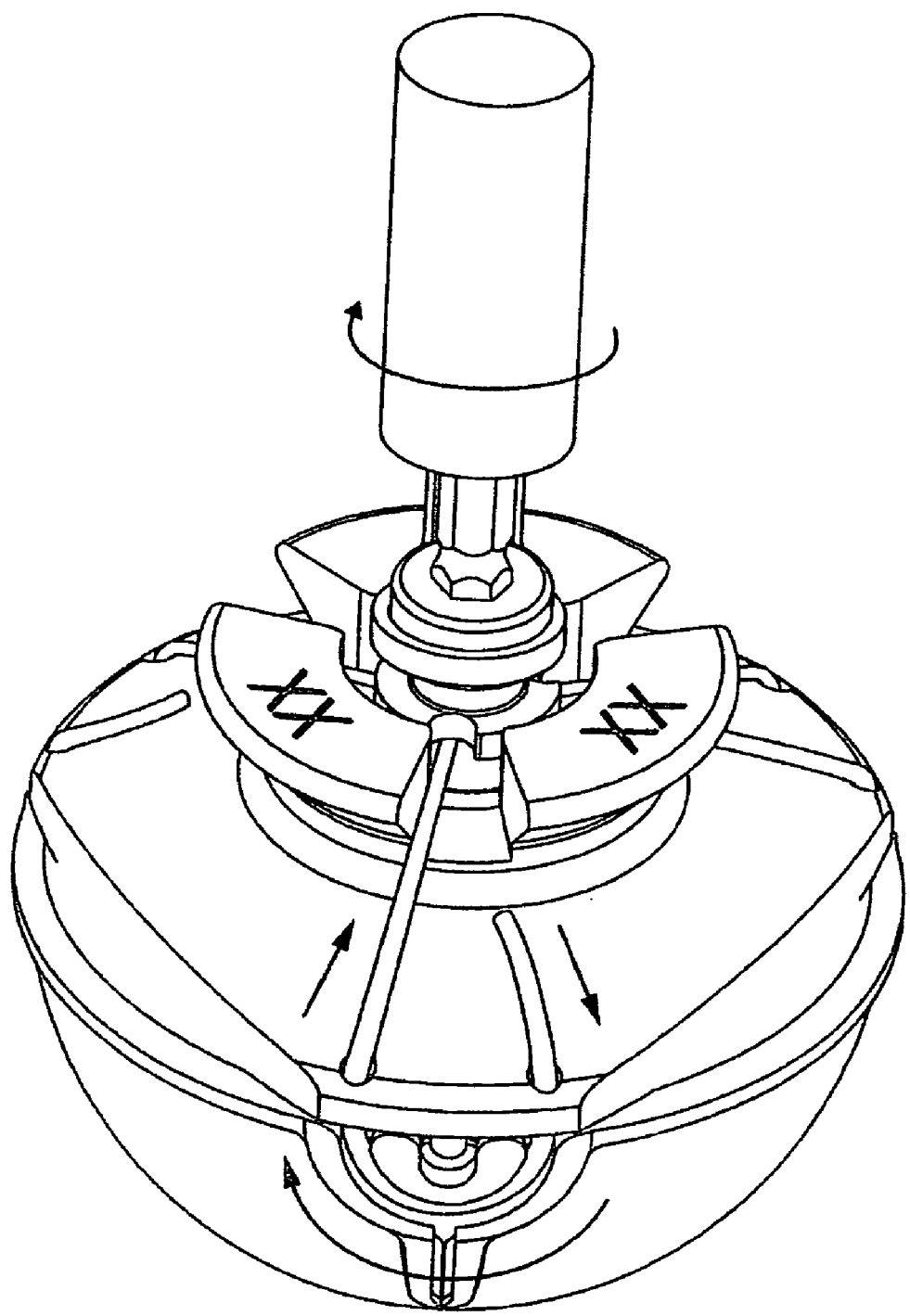
FIG. 6 illustrates the cable movement on rotation of the clamping means of FIG. 1.
Figure 7:
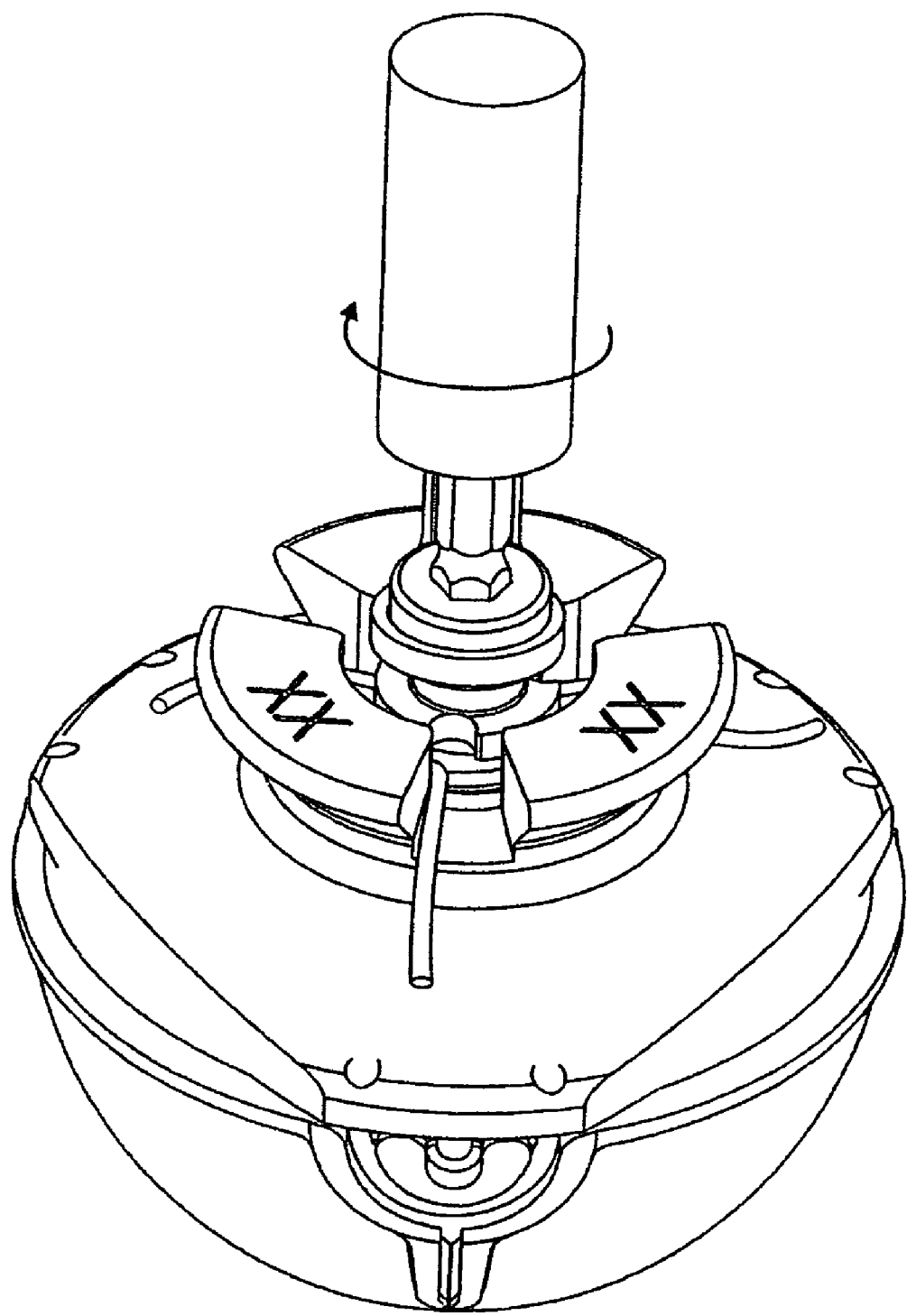
FIG. 7 illustrates the cable having been cut and the clamping means rotated.
Figure 8:
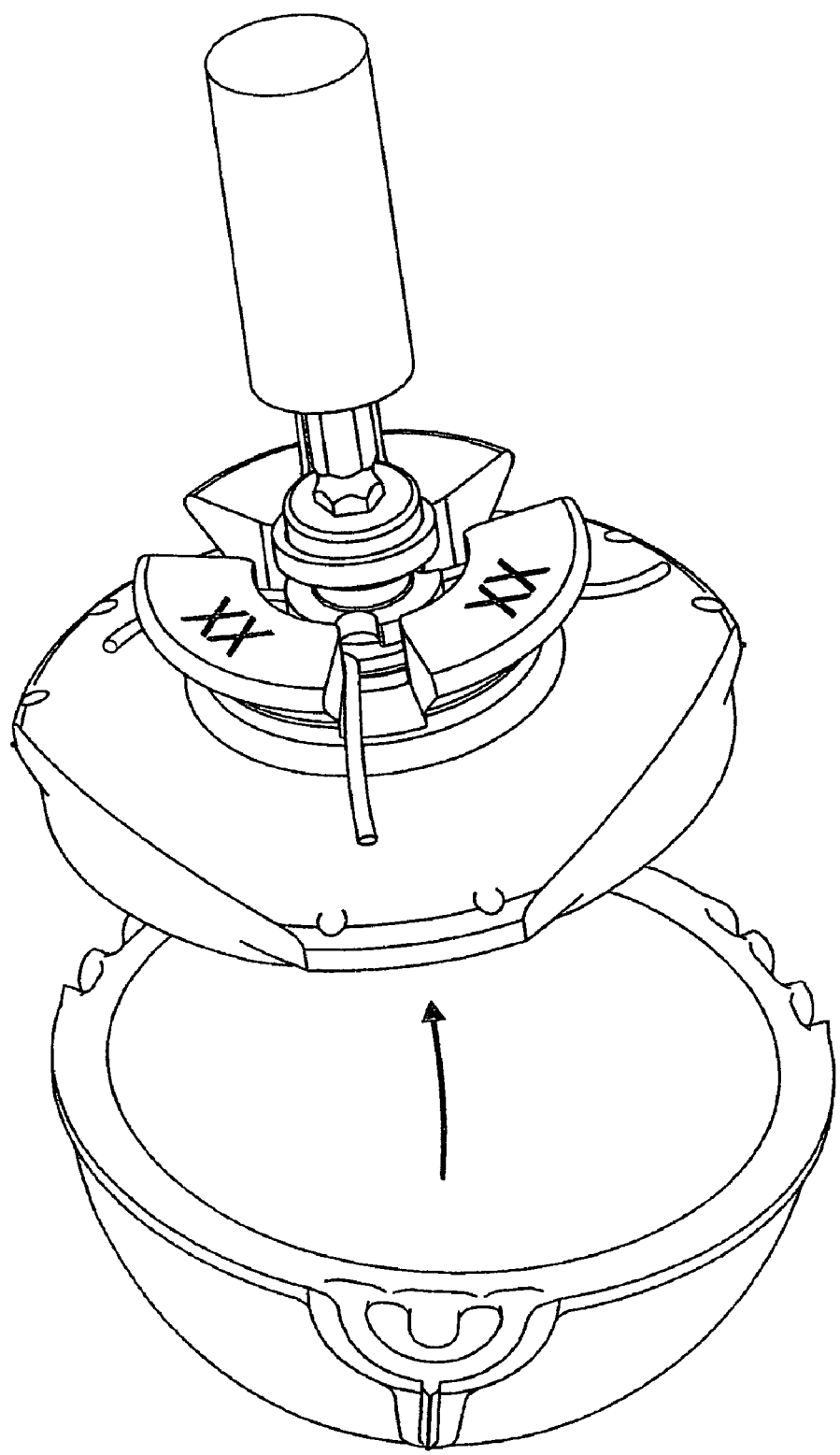
FIG. 8 represents the cap of the FIG. 1 in combination with the tool being removed from the acetabular cup prosthesis.
Figure 9D:
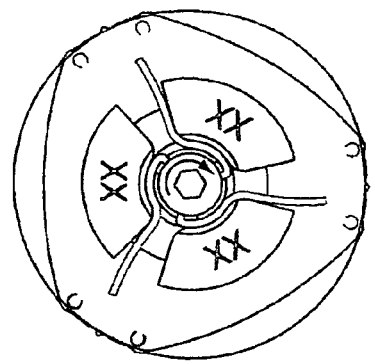
FIGS. 9*a* to *d* is a schematic view from above illustrating the action of the cable during the cutting and rotating of the apparatus.
Figure 9C:
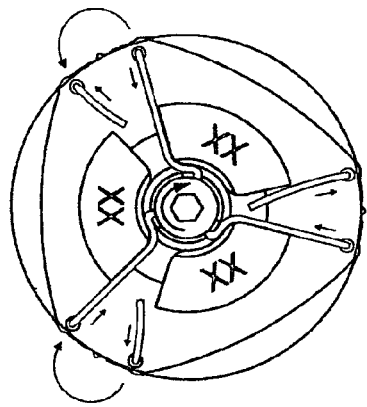
Figure 9B:
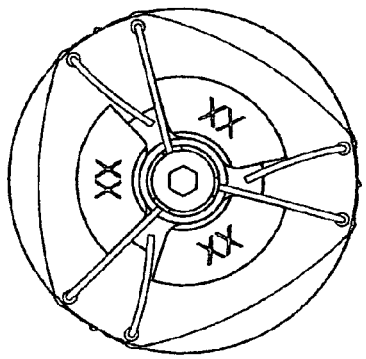
Figure 9A:
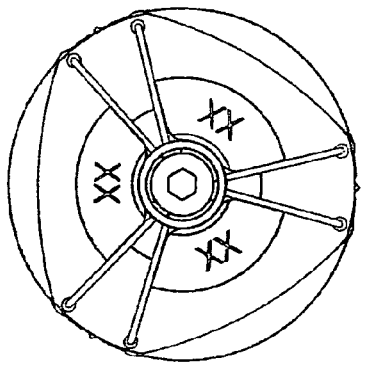

As illustrated in FIG. 6, the tool also engages with the engagement formation in the head of the nut such that when the tool is rotated the cable is wound into the centre of the cup (FIG. 7) and is thereby drawn through the track in the wall of the acetabular cup such that the entire cap can readily be removed (FIG. 8). The winding mechanism is illustrated in more detail in FIGS. 9a to 9d.

Figure 10:
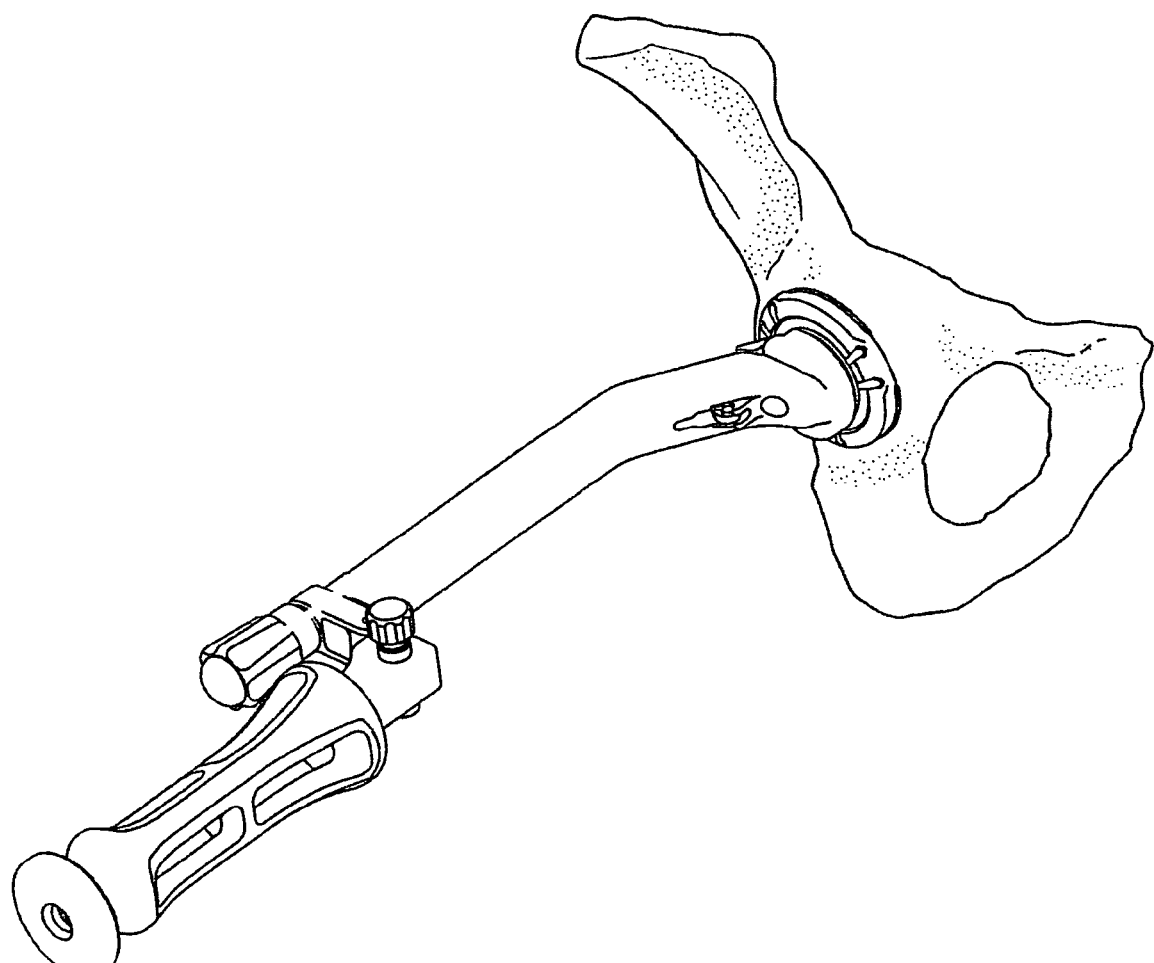
FIG. 10 illustrates the prosthesis being inserted into the pelvis using a cup introducer.

The insertion of an acetabular cup prosthesis using the cup of the present invention is described in FIG. 10.

Figure 11:
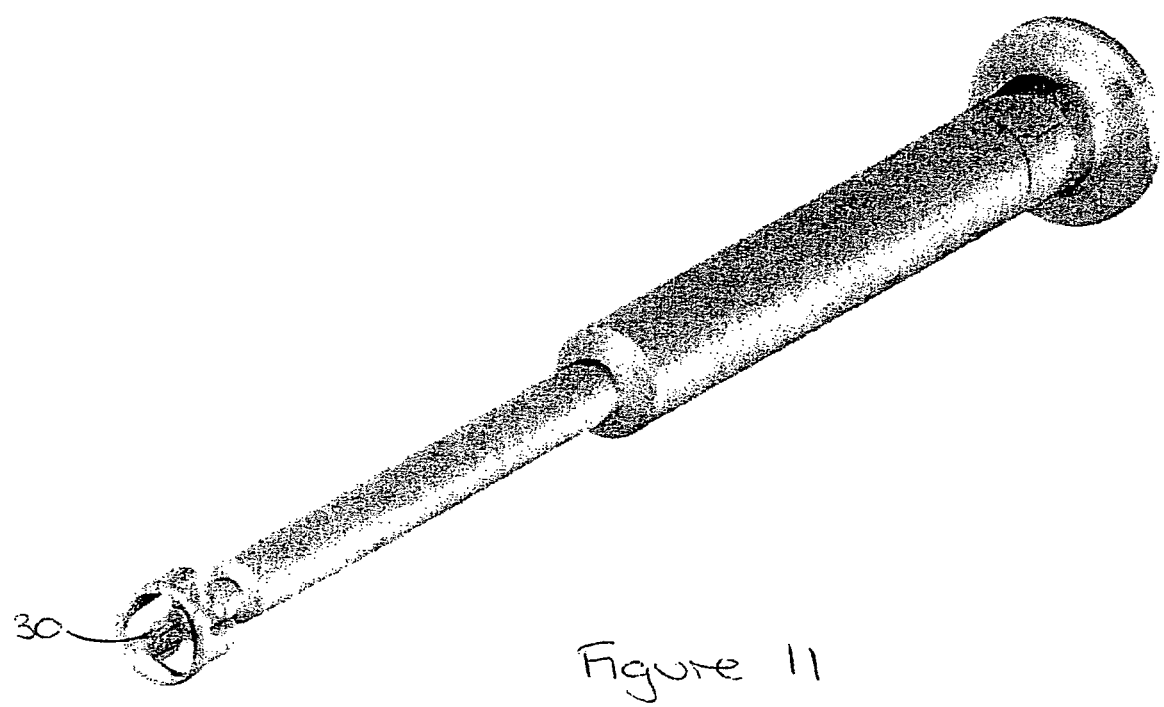
FIG. 11 illustrates an alternative tool for use with the arrangement of FIG. 1.
Figure 12:
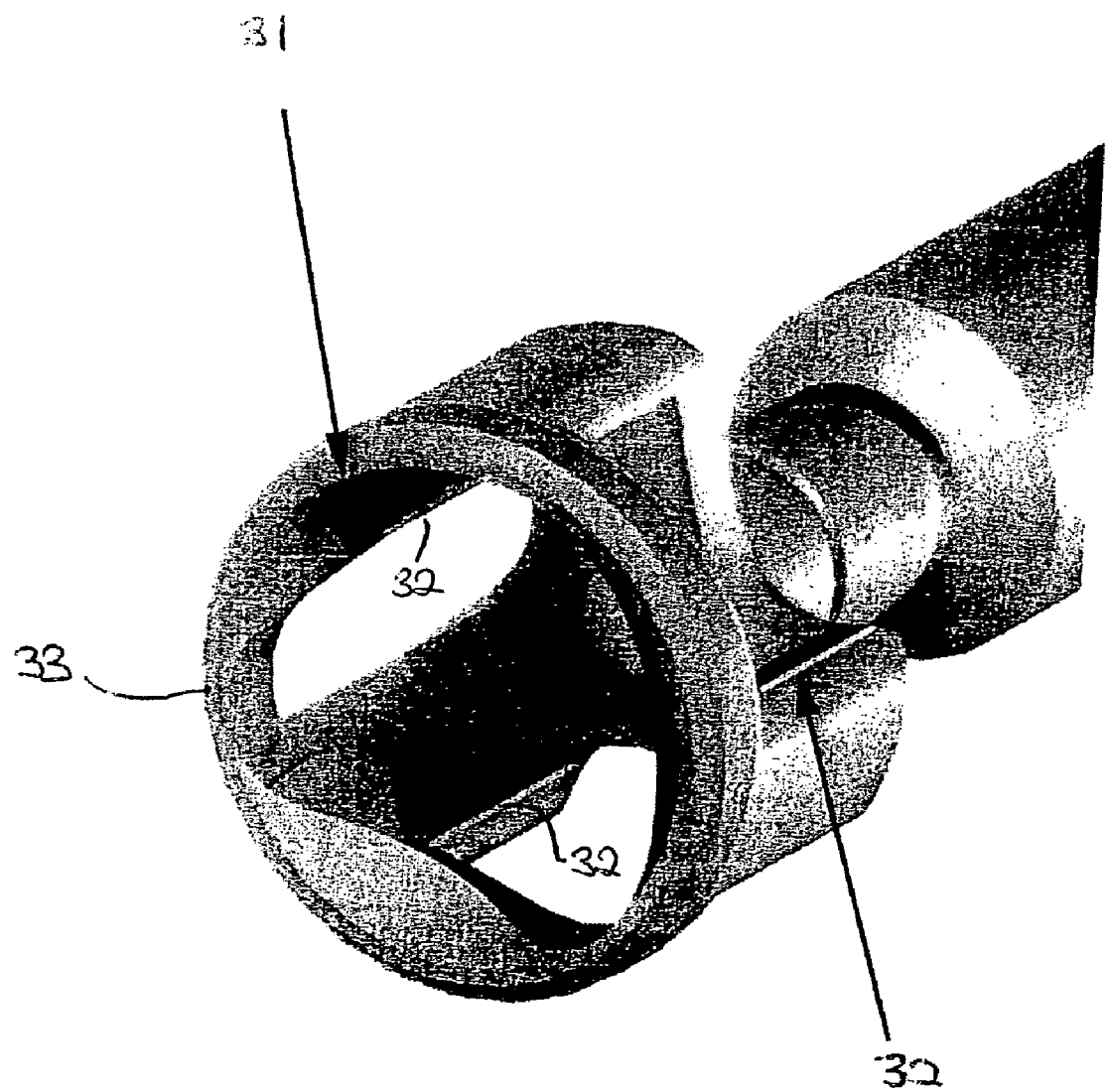
FIG. 12 is a close up of the head of the tool of FIG. 11.

An alternative tool is illustrated in FIGS. 11 and 12. Here the tool includes a socket 30 which will fit around the head of the nut 14. In this arrangement, the nut will generally have a head which has edges which can be engaged by the socket. Thus it may be, for example, hexagonal. The socket mouth may be triangular in configuration. This is the annular element which will activate the cutting means. Once cutting has occurred, the tool can be rotated such that edges 32 come into contact with the faces of the bolt head. Continued turning, will cause the clamping means to rotate. The wall 33 once rotated will hold the bolt head captive such that when the tool is withdrawn, the cap will be removed from the prosthesis.

Figure 13:
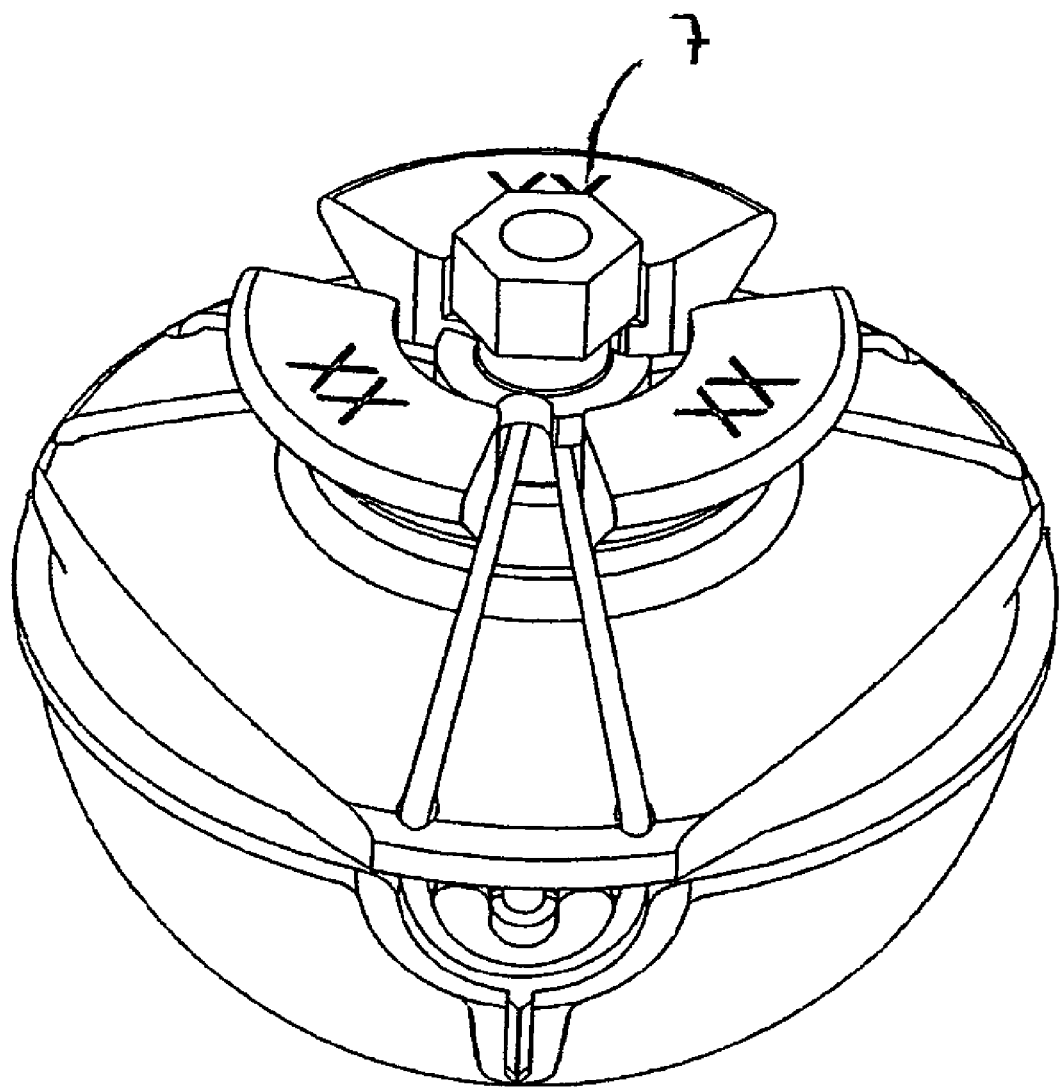
FIG. 13 is a schematic representation of a second preferred arrangement of the present invention in combination with an acetabular cup prosthesis.

An alternative arrangement of the cap is illustrated in FIG. 13. This corresponds to the cap of FIG. 1 except that the clamping means 7' is of a differing configuration to that appearing in FIG. 1. In particular, it has an external configuration of a hexagonal nut.

Figure 14:
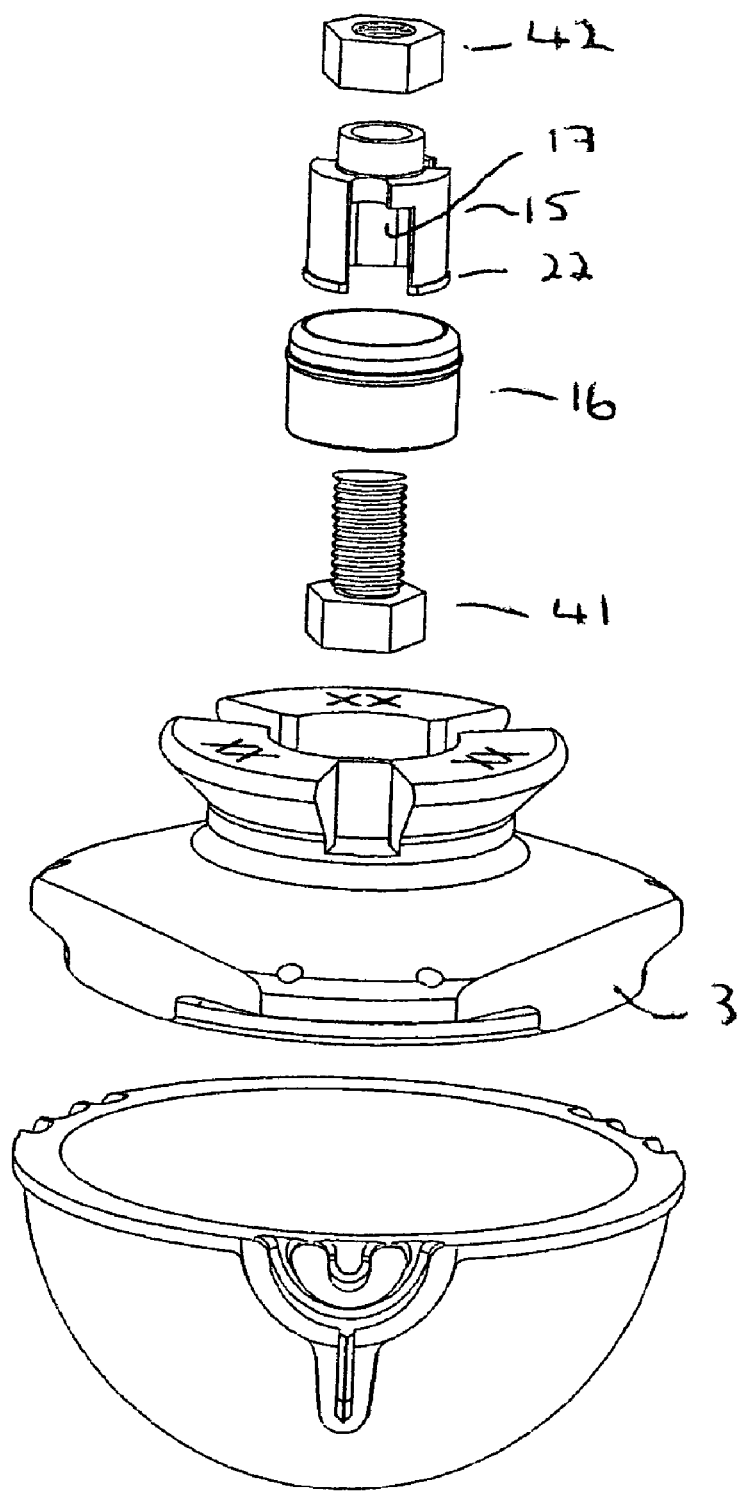
FIG. 14 is an exploded view of the components of the cap of FIG. 13.

As illustrated in more detail in FIG. 14, the clamping means comprises a nut 41 and a bolt 42. These serve to hold the cutting means within the impaction plate 3 and when the cable loops are in position to lock these within the cutting device. The cutting device comprises two components, a guillotine arrangement 15 and a collar 16. The guillotine arrangement is a sliding fit in the collar and has a skirt 22 which prevents it from being pulled through the collar. The guillotine arrangement 15 includes three blades 17 and will also be shaped such that when the guillotine arrangement moves downwardly, only one arm of the loop will be severed. It will be understood that in assembly there may be an aperture in the impaction plate such that the guillotine arrangement sits within the aperture and the bolt is applied from beneath the plate.

As in the first embodiment, during insertion, the insertion tool may connect with the neck 4 such that force is applied to the platform marked XX.

Figure 15:
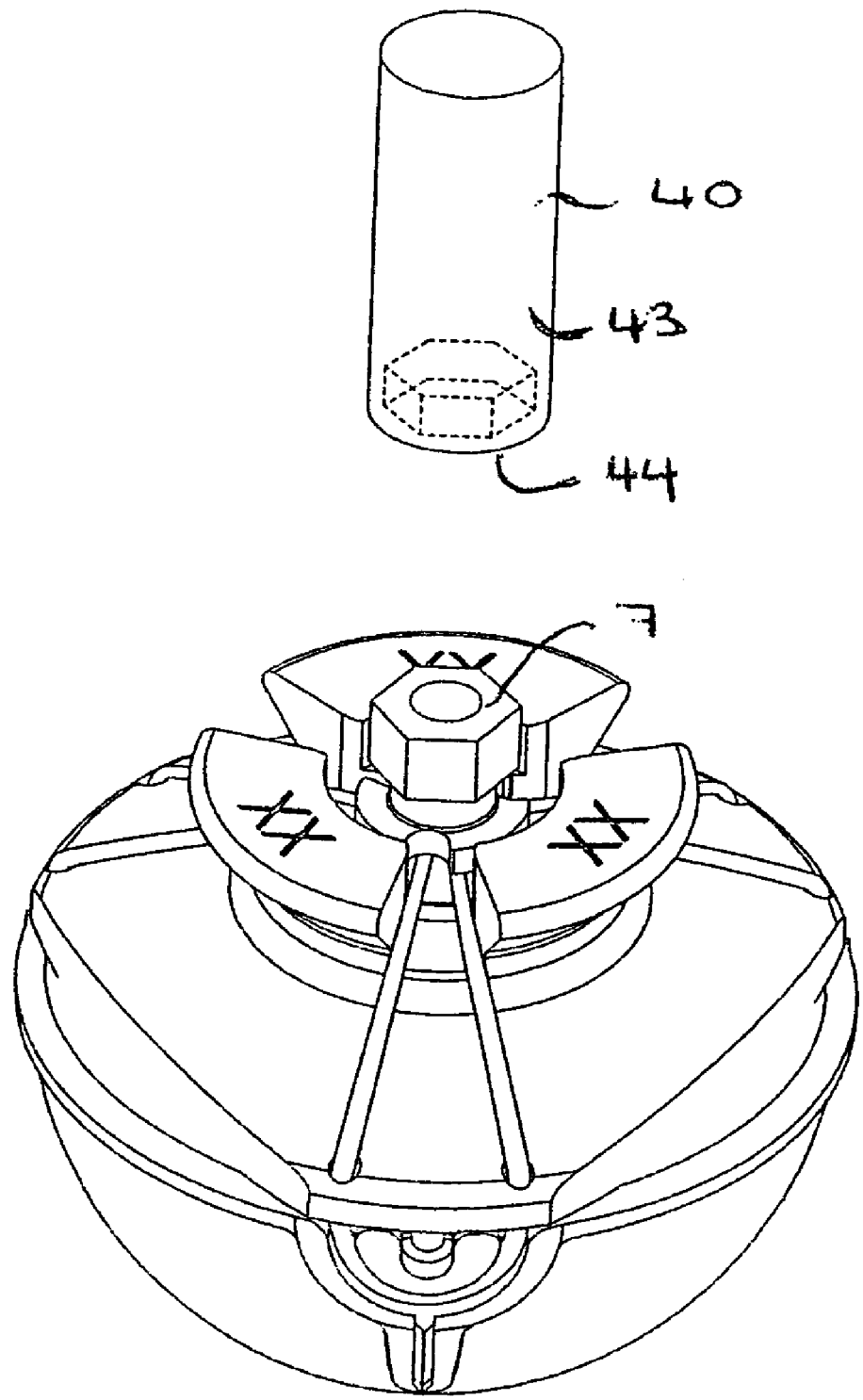
FIG. 15 is a perspective view of the cap of FIG. 13 from above illustrating the tool.

Once the acetabular cup is in the correct position, as illustrated in FIG. 15 the tool 40 which comprises a handle 43, and a female engagement formation 44 is used. The female engagement formation is of hexagonal cross-section to engage with a corresponding formation 7'.

Figures 16, 17:
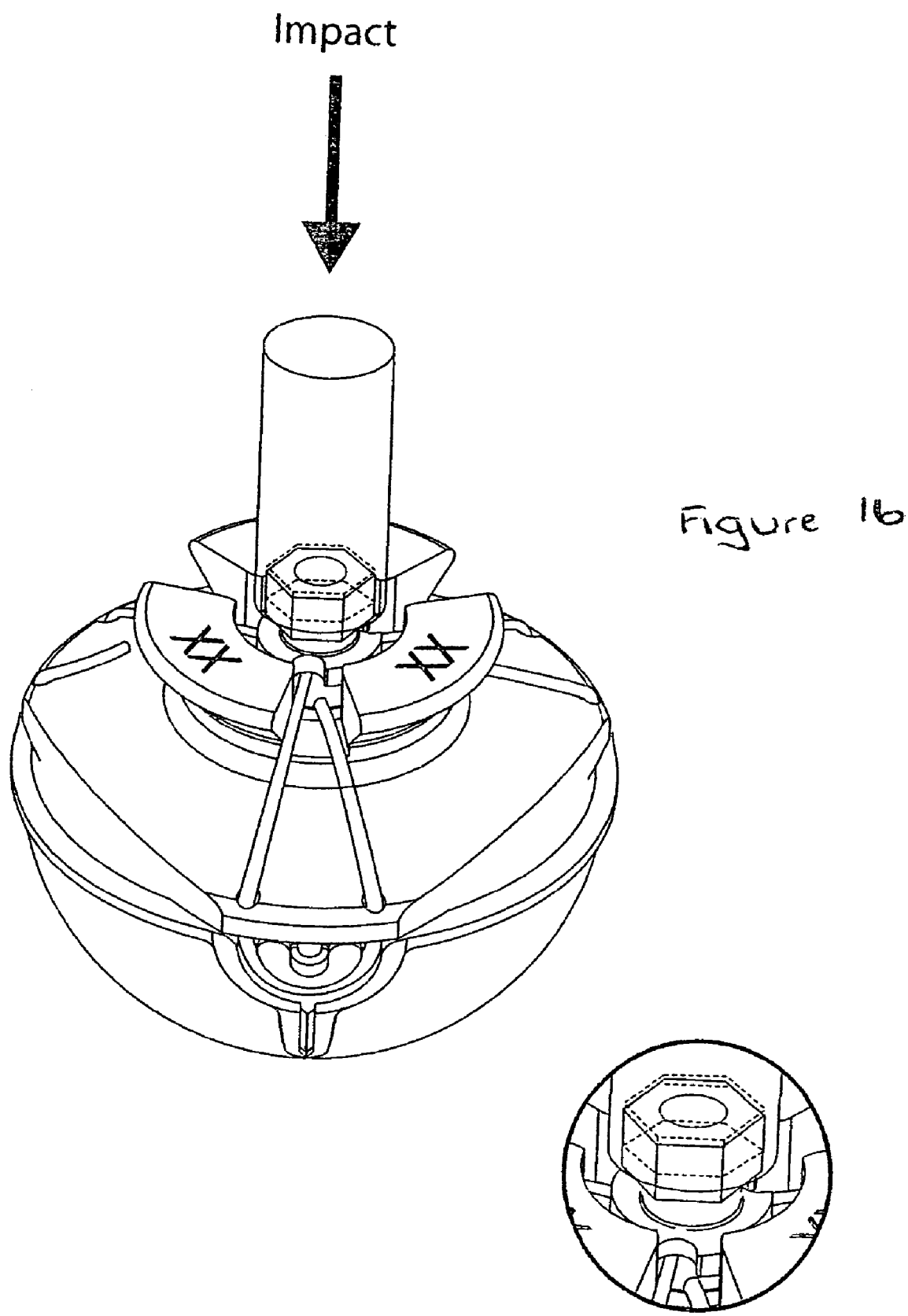
FIG. 16 corresponds to FIG. 15 with the tool engaged.
FIG. 17 represents an exploded view of a portion of FIG. 16 showing the movement of the cutting means on downward pressure on the tool.

As illustrated in FIG. 16, the tool is placed such that the annular member extends around the head of the nut such that a downward impact will force the guillotine member in a downward direction to sever the cable. This is illustrated in more detail in FIG. 17.

Generally the impact required to force the guillotine downwardly maybe substantial such that there is no risk of the cable being cut unintentionally.

Figure 18:
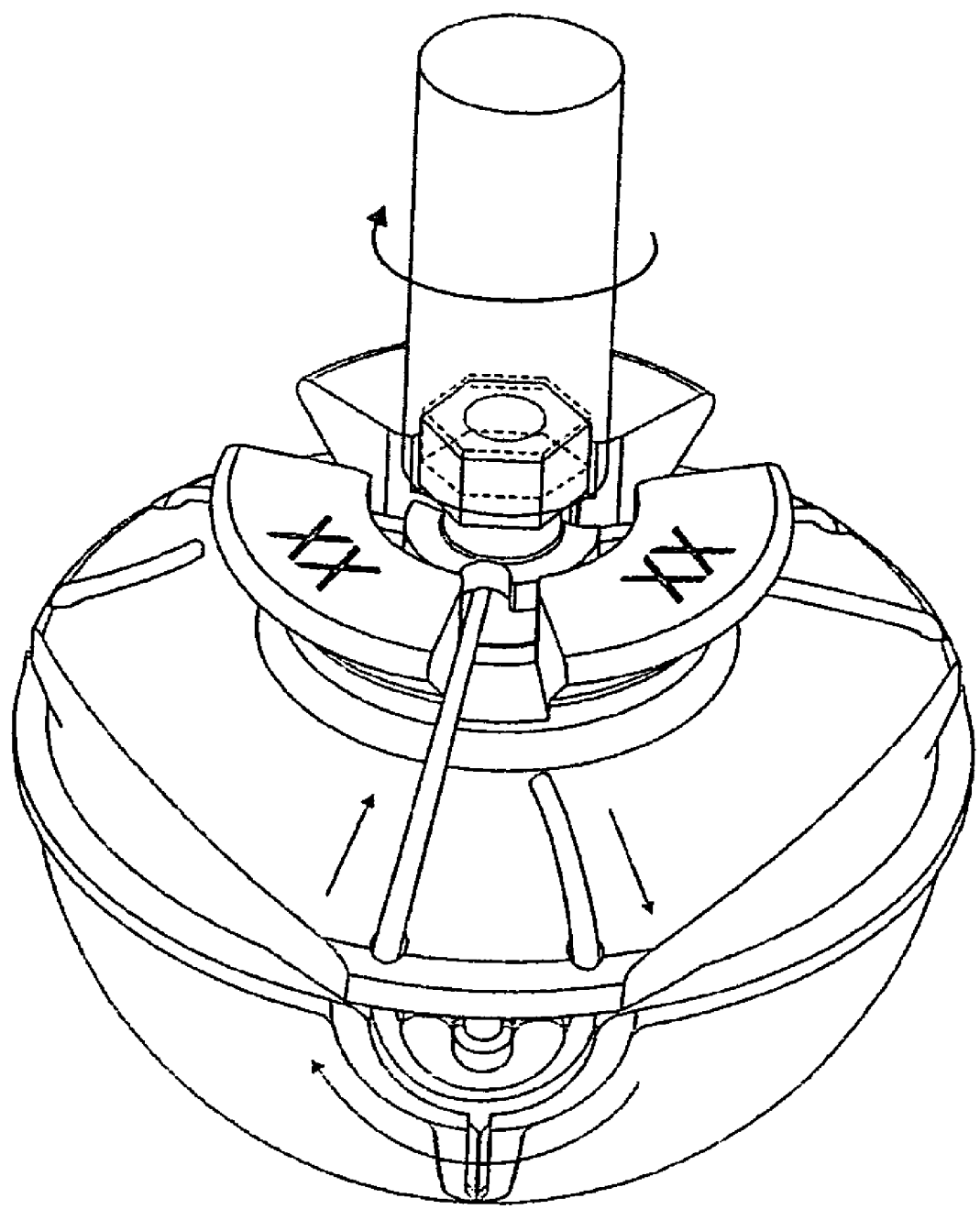
FIG. 18 illustrates the cable movement on rotation of the clamping means of FIG. 13.
Figure 19:
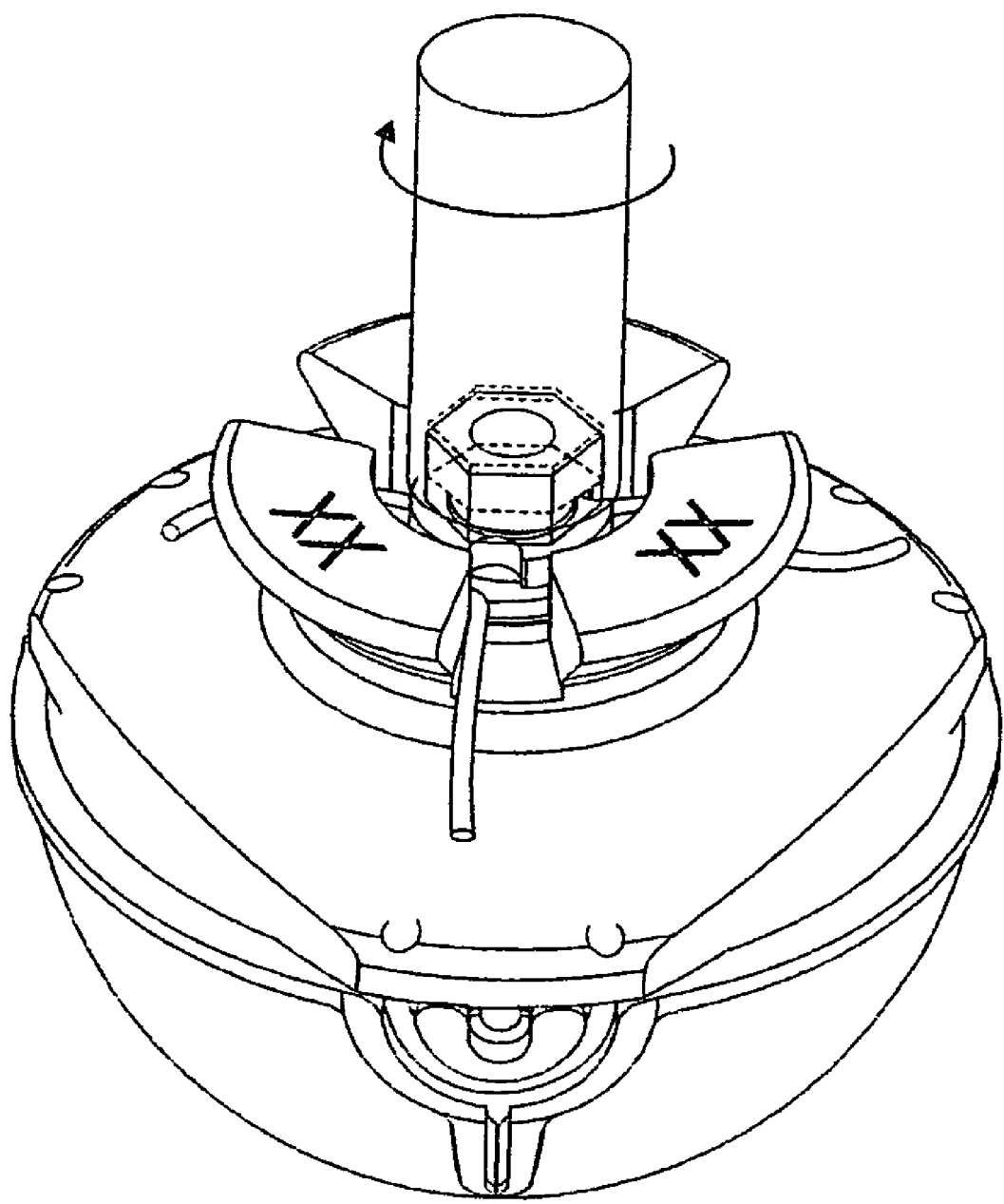
FIG. 19 illustrates the cable having been cut and the clamping means rotated.
Figure 20:
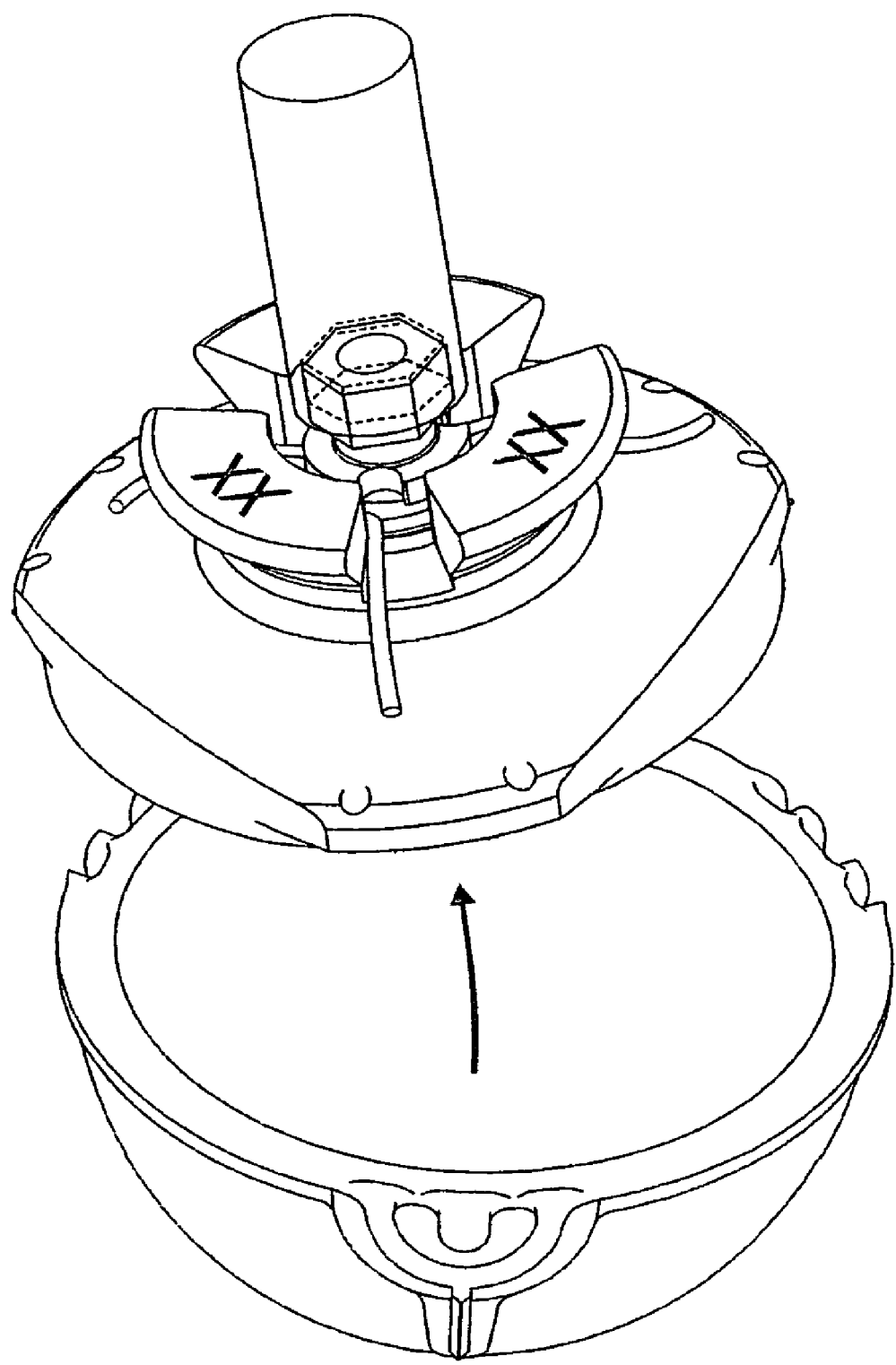
FIG. 20 represents the cap of the FIG. 13 in combination with the tool being removed from the acetabular cup prosthesis.
Figure 21D:
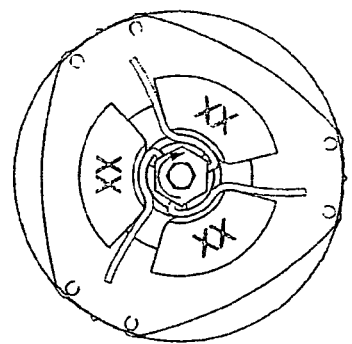
FIGS. 21a to d is a schematic view from above illustrating the action of the cable during the cutting and rotating of the apparatus.
Figure 21C:
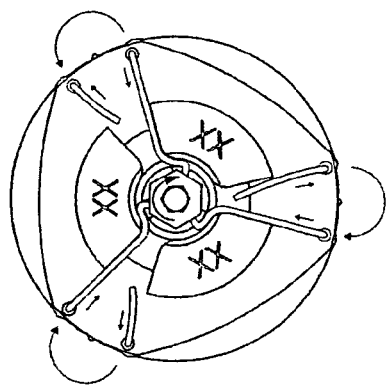
Figure 21B:
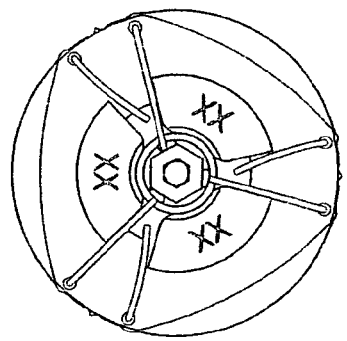
Figure 21A:
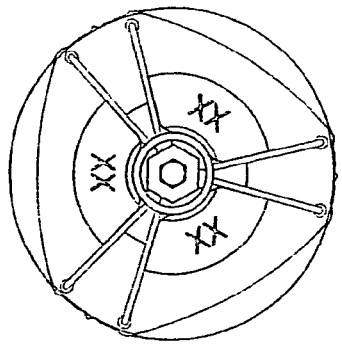

As illustrated in FIG. 18, when the tool is rotated the cable is wound into the centre of the cup (FIG. 19) and is thereby drawn through the track in the wall of the acetabular cup such that the entire cap can readily be removed (FIG. 20). The winding mechanism is illustrated in more detail in FIGS. 21*a* to 21*d*.

Figures 22, 23, 24:
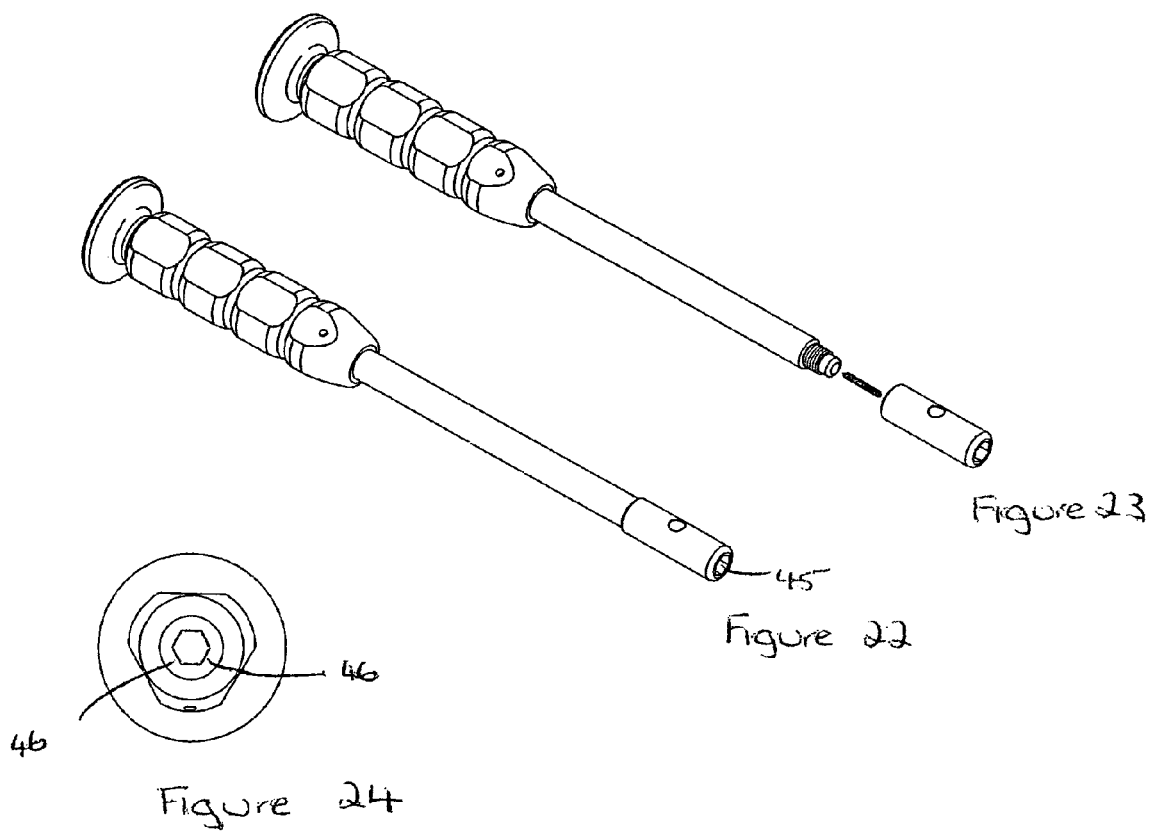
FIG. 22 illustrates an alternative tool for use with the arrangement of FIG. 13.
FIG. 23 illustrates the connection of the tip of the tool to the tip.
FIG. 24 illustrates the tool of FIG. 22 from the socket end.

A second alternative tool is illustrated in FIGS. 22 to 24. Here the tool includes a socket 45 which will fit around the 7' on the cap. In this arrangement, the nut will generally have a head which has edges which can be engaged by the socket. Thus it may be, for example, hexagonal. The edge of the socket will also operate as the annular element which will activate the cutting means.

Once cutting has occurred, the tool can be rotated such that edges 46 come into contact with the faces of the bolt head. Continued turning, will cause the clamping means to rotate.

Figures 25, 26:
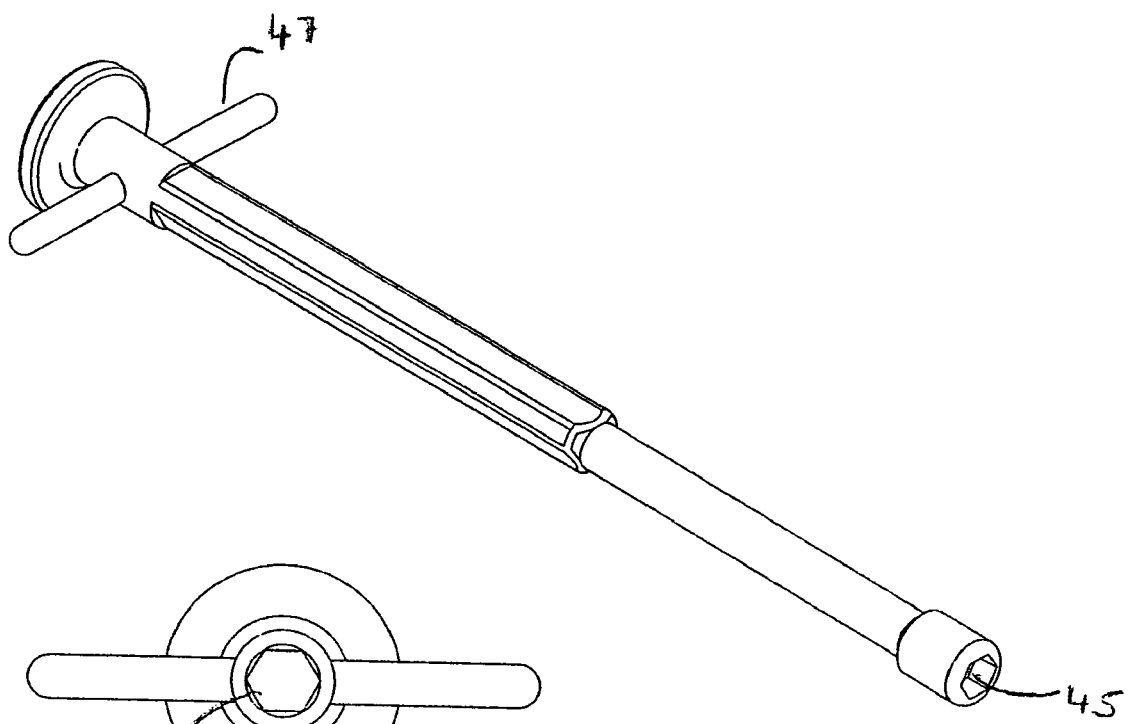
FIG. 25 illustrates a second alternative tool for use with the arrangement of FIG. 13.
FIG. 26 illustrates the tool of FIG. 25 from the socket end.

A still further tool is illustrated in FIGS. 25 and 26. This is of a similar configuration to that of FIGS. 22 to 24. A T-bar 47 is provided to facilitate the rotation of the tool.

What I claim is:

1. A cap for use during the insertion of an orthopedic cup prosthesis having an open face, comprising:
    an impaction plate configured for use during the insertion of the orthopedic cup prosthesis and configured to mate with at least a portion of the open face of the orthopedic cup prosthesis;
    at least one cable loop connectible to the impaction plate for connecting the impaction plate to the cup prosthesis;
    a clamp connected to the plate for clamping the at least one cable loop to the impaction plate; and
    a cutter connected to the plate and formed as an annular arrangement located around the clamp, said cutter moveable from a first position to a second position in which the cutter severs the at least one cable loop at a point along its length;
    wherein when the cutter is in the second position, the severed cable is retained by the clamp.

2. A cap according to claim 1 wherein the impaction plate has a disk configuration.

3. A cap according to claim 1 wherein the impaction plate includes a lip on its upper surface which, in use, extends over at least part of an edge of the prosthesis.

4. A cap according to claim 3 wherein the lip is continuous.

5. A cap according to claim 3 wherein the lip is discontinuous and, in use, extends over at least one portion of the prosthesis.

6. A cap according to claim 1 wherein the impaction plate includes a neck which extends upwardly from a surface of the impaction plate.

7. A cap according to claim 6 wherein the neck is segmented such that the cable loop passes between segments of the neck to the clamp in an arrangement where the clamp is located in a center of the neck.

8. A cap according to claim 6 wherein the neck has a generally frustoconical, annular configuration.

9. A cap according to claim 6 wherein the neck supports a platform to which, in use, an insertion tool may be attached.

10. A cap according to claim 1 wherein the impaction plate includes at least one aperture through which the cable loop passes.

11. A cap according to claim 1 wherein the cable loop comprises at least three loops.

12. A cap according to claim 1 wherein the clamp and the cutter are separate components.

13. A cap according to claim 1 wherein the clamp and the cutter are a single component capable of carrying out both functions.

14. A cap according to claim 1 wherein the cutter comprises a guillotine cutter.

15. A cap according to claim 1 wherein the clamp is located in the center of the impaction plate.

16. A cap according to claim 1 wherein the clamp is rotatable such that the cable can be wound up on the clamp.

17. A cap according to claim 1 wherein the clamp may be rotated to draw at least some of the cable into a space between the cutter and the clamp.

18. A cap according to claim 1 in combination with an activation tool for use with the cap, said tool comprising:
    a handle;
    an actuator connected to the handle for activating a cutter; and
    an engagement formation connected to the handle for engaging a clamp operatively connected to the cutter.

19. An activation tool and a cap according to claim 18 wherein engagement formation comprises a socket.

20. An activation tool and a cap according to claim 18 wherein the actuator comprises an annular ring.

21. An activation tool and a cap according to claim 20 wherein the annular ring is triangular.

22. A kit comprising:
    at least one activation tool and a cap according to claim 18; and
    at least one prosthesis.

23. A cap according to claim 1 in combination with a prosthesis.

24. A cap according to claim 23 wherein the prosthesis comprises an acetabular cup prosthesis.

25. A cap according to claim 1 wherein the loop is clamped to the plate when the cutter is in said second position.

26. A cap according to claim 1 wherein the clamp is rotatable from a first position to a second position to wind the cable about the clamp.

27. A cap according to claim 1 wherein:
    the clamp comprises a nut and a bolt; and
    the cable is clamped between the nut and the bolt.

28. A cap according to claim 1 wherein the cutter has a plurality of blades to cut at least one portion of a plurality of loops.

29. A cap for use during the insertion of an orthopedic cup prosthesis having an open face, comprising:
    an impaction plate configured for use during the insertion of the orthopedic cup prosthesis and configured to mate with at least a portion of the open face of the orthopedic cup prosthesis;
    at least one cable loop connectible to the impaction plate for connecting the impaction plate to the cup prosthesis;
    a cutter mounted on the impaction plate and constructed to receive the at least one cable loop in a first position; and
    a clamp connected to the impaction plate and to the cutter and attaching the cutter to the impaction plate, the clamp being adapted to move the cutter from the first position to a second position in which the cutter severs the at least one cable loop at a point along its length.

30. A cap according to claim 29 wherein when the cutter is in the second position, the severed cable is retained by the clamp.

* * * * *